United States Patent [19]

Takami et al.

[11] 4,322,968
[45] Apr. 6, 1982

[54] TEMPERATURE COMPENSATED PLUG-IN TYPE OXYGEN DETECTOR FOR EXHAUST GAS

[75] Inventors: Akio Takami; Toshitaka Matsuura; Tsutomu Saito, all of Nagoya, Japan

[73] Assignee: NGK Spark Plug Co., Ltd., Aichi, Japan

[21] Appl. No.: 124,023

[22] Filed: Feb. 25, 1980

[30] Foreign Application Priority Data

Feb. 23, 1979 [JP] Japan .................................. 54-23191

[51] Int. Cl.³ .......................................... G01N 27/12
[52] U.S. Cl. ..................................... 73/27 R; 338/34
[58] Field of Search .................... 73/23, 27 R; 338/34

[56] References Cited

U.S. PATENT DOCUMENTS

| | | | |
|---|---|---|---|
| 4,033,169 | 7/1977 | Fujishiro et al. | 73/23 |
| 4,208,786 | 6/1980 | Merchant et al. | 73/27 X |
| 4,222,026 | 9/1980 | Heiney et al. | 73/27 X |
| 4,244,918 | 1/1981 | Yasuda et al. | 73/27 X |
| 4,277,439 | 7/1981 | Yasuda et al. | 73/27 R X |
| 4,287,751 | 9/1981 | Yasuda et al. | 73/23 |

Primary Examiner—Kyle L. Howell
Assistant Examiner—Joseph W. Roskos
Attorney, Agent, or Firm—Sughrue, Mion, Zinn, Macpeak & Seas

[57] ABSTRACT

A plug-in type oxygen detector for detecting oxygen contained in exhaust gas is disclosed which comprises a series connected, sintered N and P type oxide semiconductors which have temperature dependencies in the same direction and respond to a partial pressure of oxygen in exhaust gas, an output being derived from a common junction of the semiconductors.

5 Claims, 5 Drawing Figures

TEMPERATURE COMPENSATED PLUG-IN TYPE OXYGEN DETECTOR FOR EXHAUST GAS

BACKGROUND OF THE INVENTION

Oxygen detectors for detecting oxygen in exhaust gas have been proposed in various forms. One example of the known oxygen detectors is composed of a ceramic substrate and a thick semiconductor membrane adhered onto one surface of the substrate. Such oxygen detectors are, however, unable to withstand the high temperature of the exhaust gas of an internal combustion engine, which is usually 200° to 900° C., and have problems of mechanical strength.

Furthermore, since the semiconductor is temperature dependent, a result of detection must later be compensated for temperature.

SUMMARY OF THE INVENTION

The present invention is intended to provide a novel plug-in type oxygen detector for detecting oxygen contained in a high temperature exhaust gas such as automobile exhaust gas, which is mechanically rigid and can withstand such high gas temperature for a practically long period of time without the necessity of later temperature compensation of the detected result.

The above object of the present invention is achieved by a detector which comprises series connected P and N type oxide semiconductors which are prepared by sintering, can respond to a partial pressure of oxygen in exhaust gas and have temperature dependencies in the same direction. An output of the detector is derived from a junction between the semiconductors, so that it is compensated for temperature. According to the present invention, the sensitivity of the detector advantageously becomes higher than those obtainable by the conventional detectors, advantageously.

That is, the oxygen detector according to the present invention comprises a pair of N and P type oxide semiconductor elements, each prepared by press-forming oxide semiconductor material powder, with dispersion of platinum powder, into a pellet, with a pair of lead wires embedded therein, and by then sintering the pellet it. The semiconductor pellets, having four lead wires, are fixedly mounted in a recess formed in one end of a ceramic column body formed with four through-holes extending therethrough, with the lead wires being inserted thereinto, respectively. Two of the lead wires derived from the other ends of the ceramic body are connected to each other so that the P and N type semiconductor pellets are connected in series. The ceramic body having the series connected semiconductors is inserted into a metal housing.

DETAILED DESCRIPTION OF THE EMBODIMENTS

Figure 1:
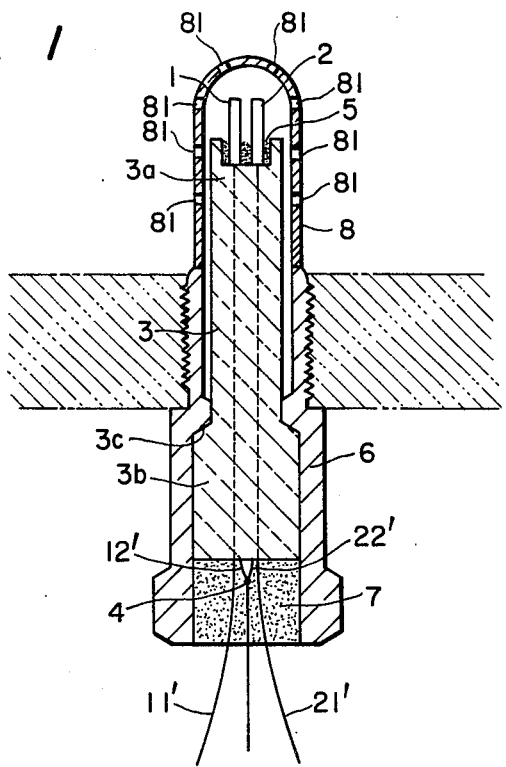
FIG. 1 is a vertical cross-section of an embodiment of the plug-in type oxygen detector according to the present invention.
Figure 2:
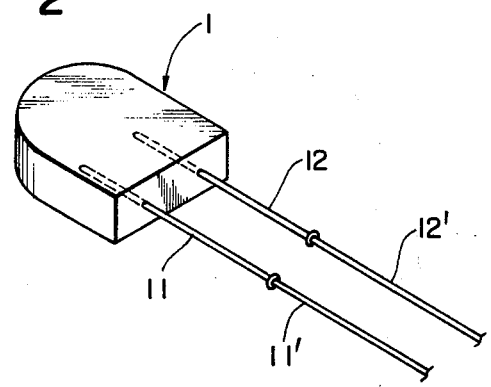
FIG. 2 is an enlarged perspective view showing one of the sintered semicondutors in the form of a pellet used in the embodiment in FIG. 1.
Figure 3:
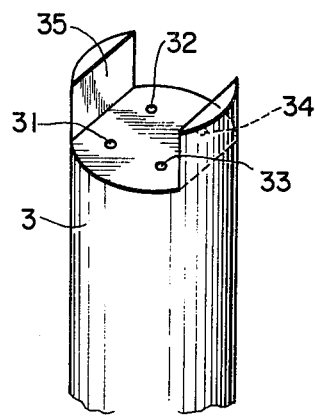
FIG. 3 is an enlarged perspective view of a top portion of the ceramic column body having through-holes.

In FIG. 1, an N type oxide semiconductor 1 is prepared by press-forming powdered N type oxide semiconductor material into a pellet, with a pair of platinum wires 11 and 12, each having a diameter of 0.3 mm, embeded therein with a predetermined distance therebetween, and by then sintering the pellet it. A pair of thermally resistant nickel wires 11' and 12' are connected to the platinum wires 11 and 12, respectively, as lead wires for the semiconductor pellet 1. A P type oxide semiconductor pellet is also similarly prepared, the size, shape and structure of which are the same as those of the N type semiconductor pellet 1. To the platinum wires of the P type semiconductor pellet 2, a pair of nickel lead wires 21' and 22' are again connected in the same manner. As the main constituent of the N type oxide semiconductor material usable in the present invention, $SnO_2$, $ZnO$, $TiO_2$, $Fe_2O_3$, $CdO$, $V_2O_5$, or $TaO_2$ etc. may be suitable. Particularly, it has been found that $TiO_2$, among others, is practically superior since the sensitivity thereof to oxygen concentration is very high, and it is stable at high temperature.

As the main constituent of the P type oxide semiconductor material, $Cr_2O_3$, $CoO$, $NiO$, $ZnO$, $LaCrO_3$ etc. are usable. Particularly $Cr_2O_3$ has resistivity and temperature dependency characteristics similar to those of $TiO_2$ and the resistivity thereof varies with oxygen concentration in a manner opposite in direction to that of $TiO_2$. Furthermore, the stability of $Cr_2O_3$ at high temperature is adequate.

Therefore, it may be advisable to use $TiO_2$ and $Cr_2O_3$ for the N type and P type semiconductor materials, respectively. In one example of the present invention, $TiO_2$ with platinum powder dispersion and $Cr_2O_3$ with platinum powder dispersion are used as raw materials for the N and P type semiconductors, respectively.

A ceramic column body 3 is formed with two pairs of through-holes 31, 32, and 33, 34 extending axially therethrough. The distance between the through-holes in each pair corresponds substantially to the distance between the platinum wires embedded in the semiconductor pellet.

The ceramic column body 3 includes a reduced diameter section 3a and a section 3b of larger diameter. A shoulder 3c is formed between the sections 3a and 3b. The purpose of the provision of the shoulder 3c will be described later. A top end of the reduced diameter section 3a of the ceramic column body 3 is formed with a recess 35 a groove and the through-holes 31 to 34 open into the bottom of the recess 35 with the through-hole pairs being disposed in parallel with the groove. The lead wires of one of the semiconductor pellets, for example, the P type semiconductor pellet 1, are inserted into the through-hole pair 31 and 32 and the lead wires of the other semiconductor pellet 2 are inserted into the through-holes 33 and 34, respectively.

Figure 4:
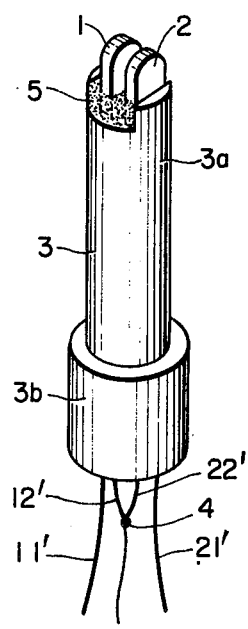
FIG. 4 is a perspective view of the ceramic column body with the semiconductor pellets being mounted.

The ends of one of the lead wires, for example, lead wire 12' of the N type semiconductor pellet 1 and one lead wire, for example, lead wire 22' of the P type semiconductor pellet 2 are commonly connected at a point 4 so that a series connection of the semiconductor pellets is established as shown in FIG. 4.

The pellets 1 and 2 are fixedly secured in the recess 35 by using a suitable thermal-resisting adhesive 5 such as inorganic cement.

Figure 5:
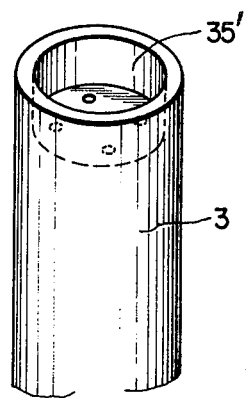
FIG. 5 shows another embodiment of the ceramic column body.

It may be possible to form the recess 35 in the form of a depression 35' as shown in FIG. 5. In such a case adhesion of the semiconductor pellets 1 and 2 thereto may become more rigid due to the existence of a surrounding wall.

The ceramic column body 3 having at one end thereof the series connected semiconductor pellets 1 and 2 is inserted into a metal housing and fixed therein by a suitable thermalresisting adhesive 7.

That is, the metal housing comprises a metal cylinder provided on an inner surface thereof with a shoulder having a shape corresponding to the shoulder 3c of the ceramic column body 3, and on an outer surface thereof with a thread to be engaged with a thread hole provided in a wall of a space (not shown) containing exhaust gas. The metal housing further comprises a metal protective cover 8 which is welded at an open end thereof to an upper end of the metal cylinder 6 as shown in FIG. 1.

The protective cover 8 is provided at a closed end portion thereof with a plurality of openings 81 for communication between the interior of the metal housing and the exhaust gas in the space.

According to the plug-in type oxygen detector constructed as above, the mechanical strength and the sensitivity of the detector are high due to the utilization of the sintered semiconductor pellets, with the aid of the utilization of the ceramic column rigidly supporting the latter and the rigid metal housing.

Further, when pure $TiO_2$ and $Cr_2O_3$ in the order of 99% or more are used for the N type semiconductor and the P type semiconductor with platinum powder dispersion, respectively, it become possible to detect oxygen in a gas having an air-fuel ratio $\lambda$ of 1 ($\lambda=1$).

What is claimed is:

1. A plug-in type, temperature-compensated oxygen detector for detecting oxygen contained in exhaust gas comprising an N type sintered single oxide semiconductor pellet, a P type sintered single-oxide semiconductor pellet, said N type semiconductor and said P type semiconductor having temperature dependencies in the same direction, a ceramic column body for fixedly supporting at one end thereof said N type semiconductor pellet and said P type semiconductor pellet, means for connecting said N type semiconductor and said P type semiconductor in series and providing output terminals at the other end thereof, and a metal housing for fixedly supporting said ceramic column body therein.

2. The oxygen detector claimed in claim 1, wherein said ceramic column body is formed at said one end thereof with a recess in which said N type semiconductor pellet and said P type semiconductor pellet are fixedly supported by using a heat resistant inorganic cement.

3. The oxygen detector claimed in claim 2, wherein said recess is in the form of a groove.

4. The oxygen detector claimed in claim 2, wherein said recess is in the form of a circular depression.

5. The oxygen detector claimed in claims 1,2,3 or 4, wherein said N type semiconductor pellet contains, as a main constituent, titanium oxide and said P type semiconductor pellet contains, as a main constituent, chromium oxide.

* * * * *